United States Patent [19]

Crawford

[11] Patent Number: 4,528,140
[45] Date of Patent: Jul. 9, 1985

[54] SYNTHESIS OF ALPHA-DITHIOPHOSPHATO AMIDES

[75] Inventor: Robert J. Crawford, Wyoming, Ohio

[73] Assignee: The Procter & Gamble Company, Cincinnati, Ohio

[21] Appl. No.: 512,299

[22] Filed: Jul. 8, 1983

[51] Int. Cl.$^3$ .............................................. C08H 3/00
[52] U.S. Cl. ................................................. 260/402.5
[58] Field of Search ............................. 260/402.5, 979

[56] References Cited

U.S. PATENT DOCUMENTS 3,660,543  5/1972  Mueller et al. ...................... 260/979
3,758,644  9/1973  Stolzer et al. ...................... 260/979

Primary Examiner—Anton H. Sutto
Attorney, Agent, or Firm—Steven J. Goldstein; Edmund F. Gebhardt; Richard C. Witte

[57] ABSTRACT

A process for synthesizing alpha-substituted O,O-dialkyl dithiophosphato amides, comprising the step of contacting a $C_8$–$C_{22}$ alpha-chloro amide with an aqueous solution of a salt of an O,O-dialkyl dithiophosphoric acid, at a temperature above the melting point of the alpha-chloro amide and in the range of from about 100° C. to about 200° C., is disclosed.

11 Claims, No Drawings

SYNTHESIS OF ALPHA-DITHIOPHOSPHATO AMIDES

TECHNICAL FIELD

The present invention relates to a process of synthesizing alpha-dithiophosphato amides whereby an alpha-chloro amide is used as the starting material. The process is carried out with water as a solvent. The process is relatively simple and inexpensive as compared to processes known heretofore. The alpha-dithiophosphato amides are useful as lubricant and fuel additives.

BACKGROUND OF THE INVENTION

Artaud et al., C. R. Hebd. Seances Acad. Sci., Ser. C (1976) 283 (11) 503-5 (C.A. 87:5424 (1977)) report on the study of cyclopropane formation from alpha-chloro esters. The cycloaddition reaction is carried out in aprotic media; tetrabutylammonium bromide is added as a catalyst.

Starks, "*Selecting a Phase Transfer Catalyst*", Chemtech 1980 (2), 110–117 discusses the use of quaternary ammonium and phosphonium salts as phase transfer catalysts. Preferred ammonium and phosphonium salts are those having at least one large alkyl group (e.g. $C_{16}H_{33}$). In general, large cations are better catalysts than small cations (e.g., the tetrabutylammonium cation is a better catalyst than the tetrapropylammonium cation or the tetramethylammonium cation).

SUMMARY OF THE INVENTION

The present invention relates to a process for synthesizing alpha-substituted O,O-dialkyl dithiophosphato amides comprising the step of contacting a $C_8$–$C_{22}$ alpha-chloro amide with an aqueous solution of a salt of an O,O-dialkyl dithiophosphoric acid at a temperature above the melting point of the alpha-chloro amide and in the range of from about 100° C. to about 200° C.

DETAILED DESCRIPTION OF THE INVENTION

Certain alpha-dithiophosphato amides have been found to be useful as antiwear additives for lubricant compositions and liquid hydrocarbon fuels, as disclosed in the pending U.S. application of Bullock et al., Ser. No. 335,435, filed Dec. 19, 1981.

The process for synthesizing the compound disclosed in the Bullock et al. Application comprises the step of converting an alpha-chloro amide to the corresponding alpha-bromo amide using lithium bromide, and the subsequent step of reacting the alpha-bromo amide with a dialkyl dithiophosphoric acid, using an alcohol as a solvent. The latter step requires approximately 18 hours to attain completion.

It has now been discovered that by the process of the present invention the alpha-chloro amide can be reacted directly with the dialkyl dithiophosphoric acid, using water as a solvent. The reaction time typically ranges from about 1½ hours to about 6 hours. The process of the present invention thus eliminates the step of converting the alpha-chloro amide to the alpha-bromo amide, thereby eliminating the use of lithium bromide. The present process further eliminates the use of an organic solvent, and reduces the overall reaction time dramatically.

In the process of the present invention, an alpha-chloro amide is contacted with a salt of a dialkyl dithiophosphoric acid at a temperature in the range of from about 100° C. to about 200° C.

The reaction is carried out with water as a solvent for the O,O-dialkyl dithiophosphoric acid salt. It has surprisingly been found that neither the O,O-dialkyl dithiophosphate nor the amide become hydrolyzed to any appreciable extent during the reaction, is spite of the presence of water and the relatively high reaction temperatures.

The O,O-dialkyl dithiophosphoric acid is present as a salt. The cation may be inorganic (e.g. sodium or potassium) or organic. Organic cations are preferred for the purpose of the present invention.

Organic cations particularly suitable for use herein are tetraalkylammonium and tetraalkylphosphonium cations. Specific examples include tetramethylammonium, tetraethylammonium, tetrapropylammonium, tetrabutylammonium, trioctylmonomethylammonium, trioctylmonoethylammonium, hexadecyltriethylammonium, and the corresponding phosphonium ions. Other suitable cations are those disclosed in Starks, "*Selecting a Phase Transfer Catalyst*", Chemtech 1980 (2), 110–117, the disclosures of which are incorporated herein by reference. Contrary to what has been found in prior art processes involving the use of quaternary cations, smaller quaternary cations are most effective in the process of the present invention. Tetramethylammonium, tetraethylammonium, tetramethylphosphonium and tetraethylphosphonium are therefore preferred for use herein.

The amount of organic cation can be varied from a catalytic amount to a stoichiometric amount. In other words, molar ratios of organic cation:dialkyl dithiophosphate ranging from about 1:100 to about 1:1 are suitable for the process of the present invention. Molar ratios in the range of from about 1:10 to about 1:1 are preferred, and most preferred are molar ratios of about 1:1.

Alpha-chloro amides can be prepared from the corresponding alpha-chloro carboxylic acid by reacting the latter with thionyl chloride and, subsequently, with ammonia, as disclosed in the Bullock et al. application at page 9, lines 1-13, incorporated herein by reference.

Alpha-chloro carboxylic acids can be obtained by the process disclosed in U.S. Pat. No. 4,148,811, issued Apr. 10, 1979 to Crawford, incorporated herein by reference. Preferred processes for preparing 1,4-bis(dicyanomethylene)cyclohexane, the precursor of the tetracyanoquinodimethane (TCNQ) catalyst used in the above process, and TCNQ itself, are disclosed in U.S. Pat. No. 4,229,364, issued Oct. 21, 1980 to Crawford, and in U.S. patent application, Ser. No. 297,881, Crawford, filed Aug. 31, 1981, both of which are incorporated herein by reference.

Of particular interest for the purpose of the present invention are alpha-chloro carboxylic acids having from 8 to 22 carbon atoms, more specifically the alpha-chlorinated fatty acids. Preferred is alpha-chlorododecanoic acid (alpha-chlorolauric acid).

The O,O-dialkyl esters of dithiophosphoric acid suitable for use in the process of the present invention are esters having from 1 to 12, preferably from 1 to 8, carbon atoms in each alkyl group. Specific examples include O,O-dimethyl dithiophosphate; O,O-diethyl dithiophosphate; O,O-diisopropyl dithiophosphate; O,O-diisobutyl dithiophosphate; O,O-dihexyl dithiophosphate; O,O-dioctyl dithiophosphate; O,O-didecyl dithiophosphate; O-methyl-O-hexyl dithiophosphate, O- ethyl-O-dodecyl dithiophosphate; and O-propyl-O-octyl dithiophosphate. Preferred is O,O-diisopropyl dithiophosphate.

Specific embodiments of the synthesis of alpha-dithiophosphato amides according to the present invention are the following:

(a) melting point of the chloro amide below 100° C.; use of water as a solvent

O,O-dialkyl dithiophosphoric acid or a water-soluble salt thereof is treated with an *aqueous solution* of a hydroxide salt of a tetraalkylammonium or tetraalkylphosphonium organic cation. Alpha-chloro amide is added, and the resulting two-phase mixture is stirred vigorously and heated to 100° C. At this temperature the chloro amide melts and exists as a water-insoluble liquid phase. The dithiophosphate salt dissolves in the liquid alpha-chloro amide, presumably aided by the organic cation, and reacts with it, forming the desired alpha-dithiophosphato amide.

(b) melting point of the chloro amide above 100° C.; use of water as a solvent

The procedure is as described hereinabove under (a), except that the reaction temperature is above 100° C. in order to melt the chloro amide. The reaction must therefore be carried out under pressure (e.g., in an autoclave) to avoid loss of the water solvent. Also reactions with chloro amides having a melting point below 100° C. can advantageously be carried out under pressure, as the reaction rate is higher at higher temperatures. Reaction temperatures above about 200° C. are undesirable because of the high pressure necessary at higher temperatures.

EXAMPLE I

Alpha-(O,O-diisopropyl dithiophosphato)lauramide was prepared as follows. The alpha-chlorolauric acid starting material was obtained by the process disclosed in U.S. Pat. No. 4,148,811, issued Apr. 10, 1979 to Crawford, incorporated herein by reference. Alpha-chlorolauric acid was converted to alpha-chlorolauramide by reaction with thionyl chloride, followed by reaction with ammonia, as disclosed in the application of Bullock et al., cited hereinabove, at page 9, lines 1–13, incorporated herein by reference.

O,O-diisopropyl dithiophosphoric acid was prepared by reacting phosphorous pentasulfide with isopropyl alcohol in benzene at 80° C., as described in the application of Bullock et al., at page 9, lines 24–33.

To 3.20 g (0.0137 mole) of the alpha-chlorolauramide were added 3.253 g (0.0152 mole) of O,O-diisopropyl dithiophosphoric acid and 10 ml of a 1.493M solution of tetraethylammonium hydroxide (0.0149 mole; obtained from Aldrich Chemical Co., Milwaukee, Wis.).

The reaction mixture was stirred vigorously, and heated in a 120° C. oil bath. An aliquot was removed after 1½ hours, added to 1N HCl, and extracted with hexane. Thin layer chromatography (TLC) showed the reaction to be nearly complete after 1.5 hours. After 3 hours of heating and stirring, the reaction mixture was poured into 1N HCl, and extracted four times with hexane. The hexane solution was washed three times with a HCl/NaCl solution, dried and evaporated; 5.28 g (94%) of a yellow oil was obtained.

The product was alpha-(O,O-diisopropyl dithiophosphato)lauramide, as confirmed by C-13 and phosphorous NMR.

The above procedure was repeated, but tetrabutylammonium hydroxide was used instead of tetraethylammonium hydroxide. Alpha-(O,O-diisopropyl dithiophosphato)lauramide was obtained in 75% yield. Its identity was confirmed by NMR.

The above procedure is carried out with the amides of alpha-chlorococonut acid, alpha-chlorotallow acid, alpha-chlorostearic acid, alpha-chloropalmitic acid, and alpha-chloroeicosanoic acid, respectively. The corresponding alpha-(O,O-diisopropyl dithiophosphato) amides are obtained.

The above procedure is further varied by reacting alpha-chloro fatty amides with O,O-dimethyl dithiophosphoric acid; O,O-diethyl dithiophosphoric acid; O,O-diisobutyl dithiophosphoric acid; O,O-dipentyl dithiophosphoric acid; O-methyl-O-hexyl dithiophosphoric acid; O-ethyl-O-octyl dithiophosphoric acid; and O-propyl-O-decyl dithiophosphoric acid, respectively. The corresponding alpha-dithiophosphato fatty amides are obtained.

EXAMPLE II

Use of a catalytic amount of organic cation.

To 1.61 g alpha-chlorolauramide (0.0069 moles) were added 2.0 ml (0.01 moles) O,O-diisopropyl dithiophosphoric acid, 2.0 ml of a 4.9M solution of NaOH (0.0098 moles), 5 ml of a 10% NaCl solution, and 0.340 g (0.001 moles) tetrabutylammonium bisulfate (obtained from Aldrich Chemical Co., Milwaukee, Wis.). The molar ratio tetrabutylammonium cation; diisopropyl dithiophosphate was 1:10.

The mixture was stirred and heated in a 120° C. oil bath. Conversion to alpha-(diisopropyl dithiophosphato)lauramide was more than 50% after one hour (TLC).

EXAMPLE III

Use of an inorganic salt of O,O-diisopropyl dithiophosphoric acid.

To 0.80 g (0.00342 moles) alpha-chlorolauramide were added 1.0 ml (0.005 moles) O,O-diisopropyl dithiophosphoric acid and 5 ml of a 1N solution of NaOH (0.005 moles).

The mixture was refluxed in a round bottom flask (120° C. oil bath), under vigorous stirring.

After 6 hours reaction time the conversion to alpha (O,O-diisopropyl dithiophosphato)lauramide was more than 50%, as evidenced by TLC.

What is claimed is:

1. A process of synthesizing alpha-substituted, O,O-dialkyl dithiophosphato amides comprising the step of contacting a $C_8$–$C_{22}$ alpha-chloro amide with an aqueous solution of a salt of O,O-dialkyl dithiophosphoric acid, at a temperature above the melting point of the alpha-chloro amide and in the range of from about 100° C. to about 200° C.

2. The process of claim 1 whereby an inorganic salt of the O,O-dialkyl phosphoric acid is mixed with an organic cation in a molar ratio organic cation:dialkyl phosphoric acid salt of from about 1:100 to about 1:1, prior to contacting the O,O-dialkyl-phosphoric acid salt with the alpha-chloro amide.

3. The process of claim 2 wherein the organic cation and the inorganic dialkyl dithiophosphoric acid salt are mixed in a molar ratio of from about 1:10 to about 1:1.

4. The process of claim 3 wherein the organic cation and the inorganic O,O-dialkyl dithiophosphoric acid salt are mixed in a molar ratio of about 1:1.

5. The process of claim 2 wherein the organic cation is a tetraalkylammonium or a tetraalkylphosphonium cation.

6. The process of claim 5 wherein the organic cation is tetraethylammonium.

7. The process of claim 1 wherein the alkyl moieties in the O,O-dialkyl dithiophosphate esters are selected from the group consisting of methyl, ethyl, propyl, isopropyl, n-butyl, isobutyl, t-butyl, and mixtures thereof.

8. The process of claim 1 wherein the alpha-chloro amide is derived from a fatty acid.

9. The process of claim 1 wherein the alpha-chloro amide is alpha-chlorolauramide.

10. A process for synthesizing alpha-substituted O,O-dialkyl dithiophosphato amides comprising the step of contacting a $C_8$–$C_{22}$ alpha-chloro amide with an aqueous solution of a tetraalkylammonium salt of an O,O-dialkyl dithiophosphoric acid, at atmospheric pressure and at a temperature of about 100° C.

11. A process for synthesizing alpha-(O,O-diisopropyl dithiophosphato)lauramide comprising the step of contacting alpha-chlorolauramide with an aqueous solution of tetraethylammonium O,O-diisopropyl dithiophosphate at atmospheric pressure and at a temperature of about 100° C.

* * * * *